(12) United States Patent
Andarawis et al.

(10) Patent No.: US 8,926,496 B2
(45) Date of Patent: Jan. 6, 2015

(54) IMPLANTABLE DEVICE SYSTEM

(75) Inventors: Emad Andarawis Andarawis, Ballston Lake, NY (US); Ertugrul Berkcan, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 527 days.

(21) Appl. No.: 13/231,025

(22) Filed: Sep. 13, 2011

(65) Prior Publication Data

US 2012/0004646 A1 Jan. 5, 2012

Related U.S. Application Data

(62) Division of application No. 12/254,851, filed on Oct. 21, 2008, now abandoned.

(51) Int. Cl.
| | |
|---|---|
| *A61F 2/00* | (2006.01) |
| *A61F 13/00* | (2006.01) |
| *A61B 5/00* | (2006.01) |
| *A61B 5/103* | (2006.01) |
| *A61B 5/117* | (2006.01) |
| *A61B 5/03* | (2006.01) |
| *A61F 5/00* | (2006.01) |
| *A61N 1/372* | (2006.01) |

(52) U.S. Cl.
CPC .............. *A61B 5/036* (2013.01); *A61B 5/0028* (2013.01); *A61B 5/6846* (2013.01); *A61F 5/0076* (2013.01); *A61B 2562/028* (2013.01); *A61N 1/372* (2013.01)
USPC .............. 600/37; 128/899; 600/561; 600/593

(58) Field of Classification Search
USPC .......... 128/899; 600/372, 373, 544–547, 549, 600/551, 558, 559, 561, 37, 300, 587, 593
See application file for complete search history.

(56) References Cited

U.S. PATENT DOCUMENTS

| | | | |
|---|---|---|---|
| 6,433,557 | B1 | 8/2002 | Rashkes et al. |
| 6,870,463 | B2 | 3/2005 | Dresti et al. |
| 7,044,911 | B2 | 5/2006 | Drinan et al. |
| 7,081,693 | B2 | 7/2006 | Hamel et al. |
| 7,209,804 | B2 | 4/2007 | Curt et al. |
| 2006/0211914 | A1* | 9/2006 | Hassler et al. .................. 600/37 |
| 2008/0024278 | A1 | 1/2008 | Volpi et al. |
| 2009/0306462 | A1* | 12/2009 | Lechner ......................... 600/37 |

* cited by examiner

*Primary Examiner* — Max Hindenburg
*Assistant Examiner* — Jonathan M Foreman
(74) *Attorney, Agent, or Firm* — Jason K. Klindtworth (57) ABSTRACT

An implantable device system is disclosed. The implantable device system comprises, a first energy transceiver system, a second energy transceiver system at least partially implanted within an organic tissue and capable of being interrogated by the first energy transceiver system, and a sensing system, wherein a state of the sensing system is available at the second energy transceiver system.

14 Claims, 7 Drawing Sheets

IMPLANTABLE DEVICE SYSTEM

This application is a divisional application of, and claims priority to non-provisional application Ser. No. 12/254,851, filed on 21 Oct. 2008, the entire contents of which are hereby incorporated by reference.

BACKGROUND

The invention relates generally to implantable devices, and more specifically to remotely interrogated implantable devices.

Certain medical conditions of the human body are controlled and/or corrected via a mechanical device implanted in the body, as opposed to a chemical "drug" route. Medical treatment of such conditions using a mechanical device can avoid possible side effects due to the ingestion of drugs.

Such devices are generally implanted within the human body close to the area where the therapeutic/corrective action is required. The overall management (monitoring and manipulation) of the state of operation of such traditionally available devices has required complicated procedures. Faulty execution of the complicated procedures can expose the patient to an infection or other medical issues. In addition, on-going post implantation management of such traditional devices usually requires direct and regular supervision by a qualified medical doctor, which limits the set of people who can derive benefit from such systems in a sustainable and cost-effective manner.

In addition, currently available implantable systems support a limited number of operation states, which limits the number of bodily conditions that can be addressed accurately. Further, most currently available implantable systems are based on invasive methods of interrogating the device such as puncturing the living tissue using a needle.

An implantable device that addresses one or more of the above drawbacks of traditionally available implantable systems would therefore be highly desirable.

BRIEF DESCRIPTION

Embodiments of the invention are directed towards an implantable device system and a method of operating the implantable device system.

An implantable device system in accordance with an embodiment of the invention includes a first energy transceiver system, a second energy transceiver system at least partially implanted within an organic tissue and capable of being interrogated by the first energy transceiver system, and a sensing system. A state of the sensing system is available at the second energy transceiver system.

An implantable device system array in accordance with an embodiment of the invention includes a plurality of transceiver systems. Each of the transceiver systems includes a first energy transceiver system, a second energy transceiver system at least partially implanted within an organic tissue and capable of being interrogated by the first energy transceiver system, and a sensing system capable of performing a measurement operation of a physical parameter. A state of the sensing system is available at the second energy transceiver system. Each of the plurality of transceiver systems is capable of independently communicating with any or all other transceiver systems of the plurality of transceiver systems.

A method of monitoring a physical parameter in accordance with an embodiment of the invention includes (a) interrogation of a second transceiver system, via electromagnetic energy, by a first transceiver system, (b) using the electromagnetic energy within the second transceiver system to perform a physical parameter measurement operation, (c) transmitting a result of the physical parameter measurement operation from the second transceiver system to the first transceiver system, and (d) optionally independently repeating steps (a), (b), or (c). The second transceiver system is at least partially implanted within an organic tissue and is capable of communication with the first transceiver system.

These and other advantages and features will be more readily understood from the following detailed description of preferred embodiments of the invention that is provided in connection with the accompanying drawings.

DETAILED DESCRIPTION

In the following description, whenever a particular aspect or feature of an embodiment of the invention is said to comprise or include at least one element of a group and combinations thereof, it is understood that the aspect or feature may comprise or include any of the elements of the group, either individually or in combination with any of the other elements of that group.

As used herein, the term "adjacent," when used in context of discussion of different parts comprising the implantable device system may refer to the situation where the parts under discussion are immediately next to each other, or it may also refer to a situation wherein intervening parts are present between the parts under discussion.

As used herein, the term "interrogation," when used in context of discussion of at least two parts of the implantable device system means that any change in an electrical, magnetic, electromagnetic, mechanical, optical, acoustic, or other physical characteristic of one part is detectable and measurable via the other part.

As used herein, the term "energy transceiver" refers to any device that has both a transmitter and a receiver. The device, circuitry and/or housing of the transmitter and receiver can be shared or can be independent. The energy transceiver device can include one or more transponder, and/or one or more transceiver, and/or one or more transverter. Said energy transceiver can include an electromagnetic radiation transceiver, an acoustic energy transceiver, and radiation transceiver, a vibration energy transceiver, a mechanical energy transceiver, and combinations thereof.

As used herein, the term "organic tissue" refers to any biological tissue. As used herein, the term "patient" refers to any living entity, for example, animals and human beings. Typically, the term "organic tissue" will be used to refer to any biological tissue from which the "patient" is composed.

As used herein, the term "biocompatible material" refers to any natural or man-made material that comprises a whole or a part of an organic tissue, or of a biomedical device, such as an implantable device system, wherein the device system performs and/or augments and/or replaces a natural function of the organic tissue and/or is not rejected by the body's immune system and/or is not harmful to the body or tissue.

As used herein, the term "active component," when used in the context of discussion of one or more parts of the implantable device system means that the part requires a source of energy in order to be able to perform its function. As used herein, the term "passive component," when used in the context of discussion of one or more parts of the implantable device system means that the part does not require a source of energy in order to be able to perform its function.

As used herein, the term "reference controller" when used in the context of discussion of one or more parts of the implantable device system is an element that controls whether a reference element is or is not incorporated within the sensing operation of a physical quantity.

Figure 1:
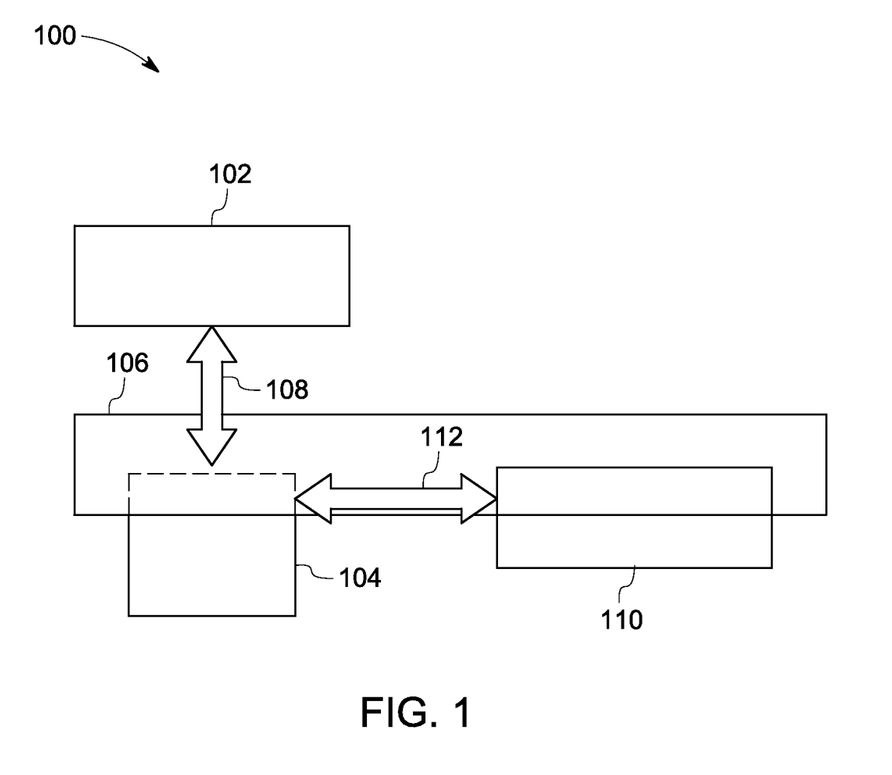
FIG. 1 is a schematic representation of an implantable device system in accordance with an exemplary embodiment of the invention.

In accordance with an embodiment of the invention, an implantable device system 100 is shown schematically in FIG. 1. The implantable device system 100 includes a first energy transceiver system 102, a second energy transceiver system 104 at least partially implanted within an organic tissue 106 and capable of being interrogated, via interrogation channel 108, by the first energy transceiver system, and a sensing system 110, wherein a state of the sensing system 110 is available, via a sensing channel 112, at the second energy transceiver system 104 through the organic tissue 106. The first energy transceiver system 102, and/or the second electromagnetic transceiver system 104, and/or the sensing system 110, comprise active components, or they may comprise passive components or combination thereof.

In one embodiment of the invention, the first energy transceiver system 102 and the second energy transceiver system 104 have the ability for two-way energy exchange, over a distance, between each other. The energy may be electromagnetic energy and may be used for the purpose of communication, or it may contain, possibly in encoded form, a value of a measured physical parameter. In certain embodiments, the exchanged energy may be stored within the first and/or of the second energy transceiver systems 102 and 104. Further, the exchanged energy may be used for energizing one or more components of the first and/or of the second energy transceiver systems 102 and 104. Further the exchange of energy may be in the form of an energy reflection wherein the characteristics of this energy has been modified by the value of the measurand. In one embodiment, the distance between the first energy transceiver system 102 and the second energy transceiver 104 system is about 15 centimeter (cm). In one embodiment, the distance between the first energy transceiver system 102 and the second energy transceiver system 104 is about 1 cm, when for example, the implantable device system is implanted close to the skin surface. In yet another embodiment, the distance between the first energy transceiver system 102 and the second energy transceiver system 104 is about 15 cm, when for example at least a part of the implantable device system is implanted or attached to an internal organ.

The energy exchange between the first energy transceiver system 102 and the second energy transceiver system 104 may be electromagnetic energy belonging to any region of the electromagnetic energy frequency spectrum. Non-limiting examples of the regions include microwave, radiowave, visible, infra-red, X-ray, gamma, and combinations thereof. Further, the energy exchange between the first energy transceiver system 102 and the second energy transceiver system 104 may be via acoustic, or vibrational energy. When the energy exchange is acoustic or vibrational the energy can belong to the ultrasonic or lower frequency ranges. In addition, the energy is being used for interrogation, it may be transmitted as an analog signal. Further, the electromagnetic energy may be frequency modulated, amplitude modulated or phase modulated and may further include a carrier electromagnetic energy wave. In one embodiment of the invention, the energy transfer between the first energy transceiver system 102 and the second energy transceiver system may be by mechanical energy. Non-limiting examples of the types of mechanical energy include sound energy and ultrasound energy and vibrational energy. Energy transfer schemes that employ a combination of electromagnetic and mechanical energies also fall within the purview of embodiments of the invention.

The implantable device system 100 can be fabricated in a variety of embodiments, depending upon its intended functionality. For instance, in one embodiment of the invention shown in FIG. 2, a second energy transceiver system 200 is housed at least partially within a biocompatible packaging 201 and includes a physical parameter sensing system 202. In the illustrated embodiment, the physical parameter sensing system 202 includes a physical interface member 204 and a sensor 206. The physical interface member 204 can communicate with the sensor 206 via channel 203. The physical parameter sensing system 202 has the ability to perform, via the physical interface member 204 and the sensor 206, a sensing function of one or more physical parameter 210. The one or more physical parameter 210 is available at the physical interface via channel 231. An analog reading produced as a result of the sensing function is communicated to at least one energy transformer 211, via at least one channel 207. Each of the at least one energy transformer 211 in turn comprises at least one data interface module 208 and at least one transducer element 214, together with at least one channel 212 for communication between the at least one data interface module 208 and the at least one transducer element 214. Non-limiting examples of physical parameters 210, which may be measured via the physical parameter sensing system 202, include physiological variables such as pressure, temperature, pH, electromagnetic energy, given chemical species, or mechanical parameters such as displacement, deformation, and strain, or combinations thereof. The components of the physical parameter sensing system 202 each may be active or passive components.

Figure 2:
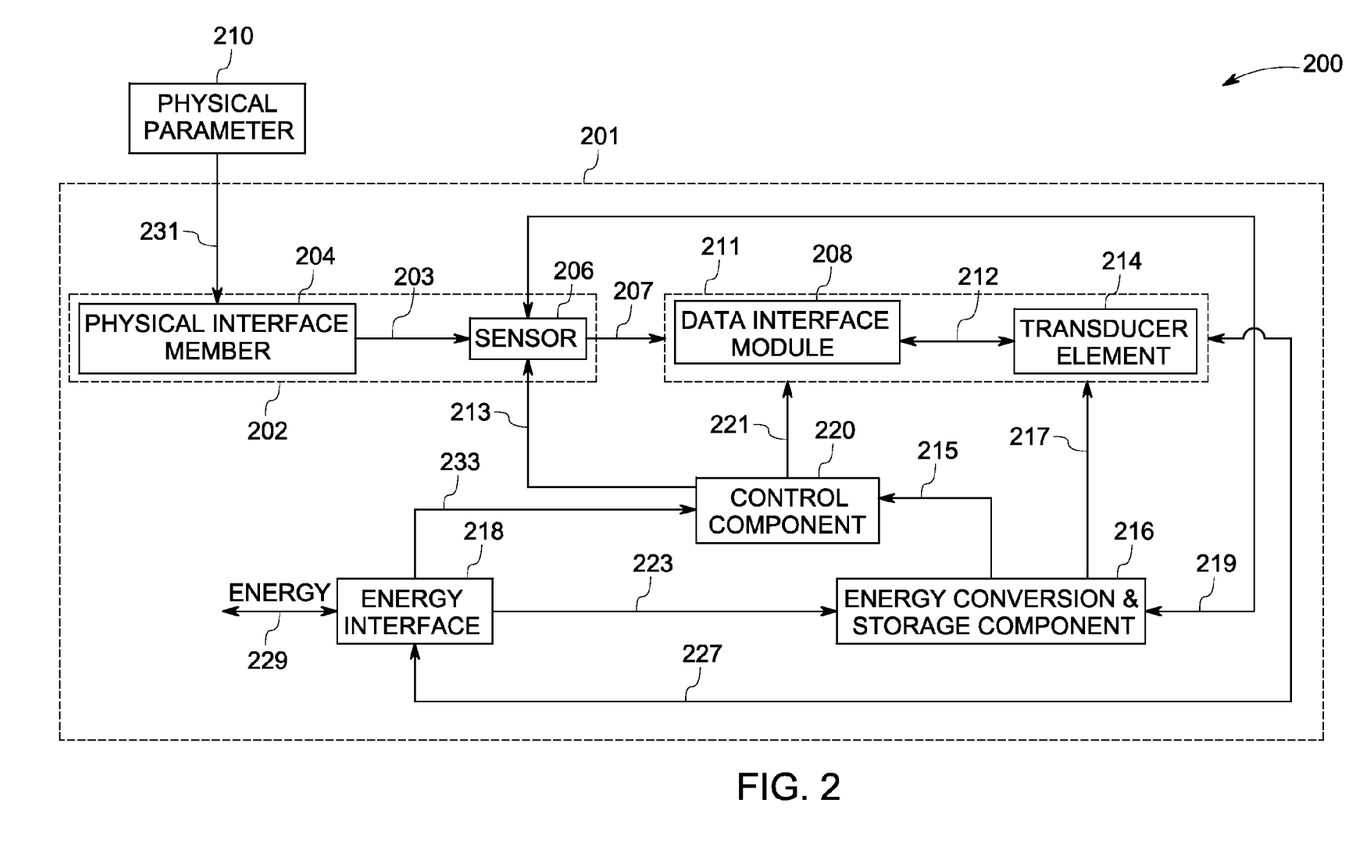
FIG. 2 is a block-diagram representation of a second energy transceiver system for use in the implantable device system of FIG. 1.

The physical interface member 204 can be any suitable member that provides an interface to the environment. The one or more physical parameters 210 characterize what needs to be sensed, and the sensor 206 performs the operation of sensing the one or more physical parameters 210. In one embodiment of the invention, the physical interface member 204 may include a membrane, a pressure transfer element such as a diaphragm, a pressure conversion element, a temperature transferring element such as a heat pipe, a permeable membrane, one or more ion-selective electrodes, an electromagnetic antenna, or combinations thereof. Such a membrane may permit a selective transport of materials across itself. Further such membranes may contain auxiliary parts that provide, for instance, mechanical support. Suitable examples of materials from which such any physical interface member may be composed, include, but are not limited to, silicon, titanium glass, metal, ceramic, polymer, semiconductor, biocompatible materials, or other materials housed in biocompatible materials.

Non-limiting examples of possible types of sensors 206 include capacitive sensors, piezoelectric sensors, thermal sensors, inductive sensors, resistive sensors, mechanical sensors, or combinations thereof. The sensors 206 may be monolithic or distributed in space. Further, the sensors may be biased and measured by way of a direct current (DC) technique, or an alternating current (AC) technique, or a combination of DC and AC techniques. It is possible that the bias level to the sensor 206 may be one of the factors determining the sensing characteristics such as selectivity and/or sensitivity and/or range of operation towards one or another physical parameter 210. The AC and/or DC bias used in the operation of the sensor 206 may be an electrical current, an electrical voltage, or a combination thereof. Further, the AC or DC response of the sensor 206 during operation of the sensor 206 may be an electrical current, an electrical voltage, or a combination thereof. Typically, the sensor 206 makes available a result of the sensing function performed by it, as an analog reading. It is pointed out that the sensor 206 may be employed to perform quantitative or qualitative sensing function of the given one or more physical parameters 210.

In one embodiment of the invention, the sensor 206 includes a micro-electro-mechanical system (MEMS) sensor selected from the group consisting of MEMS based pressure sensors, MEMS incorporating circuit elements, and combinations thereof. It is likely a sensor 206, when constructed as a MEMS sensor, may offer additional advantages such as, reduced size, reduced energy consumption, reduced cost, high level of integration, amongst other advantages.

In one embodiment of the invention, the data interface module 208 is tasked with converting the analog reading, obtained as a result of the sensing function performed by the sensor 206, to an equivalent processed reading that is in a format that is acceptable to a transducer element 214. The processed reading may be in an analog format and communicated to the transducer element 214 through the channel 212. The channel 212 may also allow for two-way communication between the data interface module 208 and transducer element 214. In one embodiment of the invention, the data interface module 208 may perform a thresholding operation wherein the analog reading, obtained as a result of the sensing function performed by the sensor 206, is converted to one or more processed discrete reading that is in a format that is acceptable to the transducer element 214.

In one embodiment of the invention, the data interface module 208 includes a variable capacitor, a reference capacitor, a distributed capacitor, an inductor, a variable inductor, a reference inductor, a switch, passive elements, and combinations thereof. The passive elements can include mechanical elements such as springs.

In one embodiment of the invention, the second energy transceiver system 200 further comprises an energy conversion and storage component 216 (discussed below), an energy interface 218, and a control component 220. In one embodiment of the invention, the energy interface 218 is an energy transceiving antenna. In one embodiment of the invention, the control component 220 includes a switch controller, or a position controller, or a reference controller, or combinations thereof.

The transducer element 214 is capable of accepting an input quantity, and producing an output quantity that is a function of the input quantity. The transducer element 214 may be any device that has the capability to accept, when provided in a suitable form, a result of a sensing operation performed by the physical parameter sensing system 202 as an input quantity via the data interface module 208 and channel 212. The control component 220 has the capability to interrogate, via a channel 221, the energy transformer 211 for the output quantity produced by the transducer element 214. The energy conversion and storage component supplies energy to the control component 220 via line 215. In one embodiment, the transducer element 214 is a passive component and does not require energy from an energy conversion and storage component 216 to perform its functions. The transducer element 214 may include one or more components that allow for a control of the relationships between the signal that it receives as input and the signal that it generates as output. The choice of the type of transducer element 214 may be based on the specific requirements of the particular function that the implantable device system 100 is tasked to perform. The transducer element 214 can be any element capable of converting one form of electromagnetic energy to another form of electromagnetic energy. Non-limiting examples of the transducer element 214 are an inductor, a capacitance, an optical energy to electrical energy converter, a mechanical energy to electrical energy converter, magnetic energy to electrical energy converter and combinations thereof.

Non-limiting examples of the input quantities that are acceptable to the transducer element 214 are impedance, capacitance, inductance, and resistance. In one embodiment, the transducer element is capable of producing output quantities proportional to the aforementioned input quantities. Non-limiting examples of the output quantities are impedance, capacitance, inductance, and resistance.

In one embodiment of the invention, the second energy transceiver system contains a channel 213 that allows the control component 220 to communicate directly with the sensor 206. In one embodiment, the channel 213 serves as an "autocompensation enable" channel.

The energy conversion and storage component 216 provides energy to all the active components within the implantable device system. In one embodiment of the invention, the second energy transceiver system 200 contains lines 215, 217 and 219 that aid the energy conversion and storage component 216 to provide energy to the control component 220, energy transformer 211, and the sensor 206 respectively. The energy conversion and storage component 216 has the capability to receive, and/or convert, and/or store, and/or transfer energy in a variety of forms. For instance, the energy conversion and storage component 216 may receive energy 229, via line 223, from the energy interface 218, in the form of electromagnetic energy, and it may convert the same into chemical energy by charging a rechargeable battery. In the instant example, the charging of the rechargeable battery is equivalent to storing the electromagnetic energy within the rechargeable battery. This stored energy may be made available, as and when required, to the active components. It is pointed out that another "energy conversion" step may be required to convert the stored energy into a form that is acceptable to the given active component. It is further pointed out that the energy conversion and storage component 216 may be a monolithic component, or it may be a distributed component.

The energy interface 218 can be used to transmit information in the form of electromagnetic energy to the first energy transceiver system 102. In one embodiment, the energy interface 218 also has the ability to receive energy, such as for instance, from the first energy transceiver system 102. The energy interface 218 is capable of communicating with the control component 220 via channel 227. The choice of the type of energy interface 218 is determined by a variety of factors, such as the type and amount of information that the energy interface 218 is tasked to transmit, or the specific characteristics of the first energy transceiver system 102, such as, for instance, its ability to receive information against a noisy background and choice of frequencies that it may use for communication. The energy interface 218 is also capable of two-way communication with the energy transformer via line 227. In one embodiment, the energy interface 218 is also capable of communicating with the control component via line 233.

Figure 3:
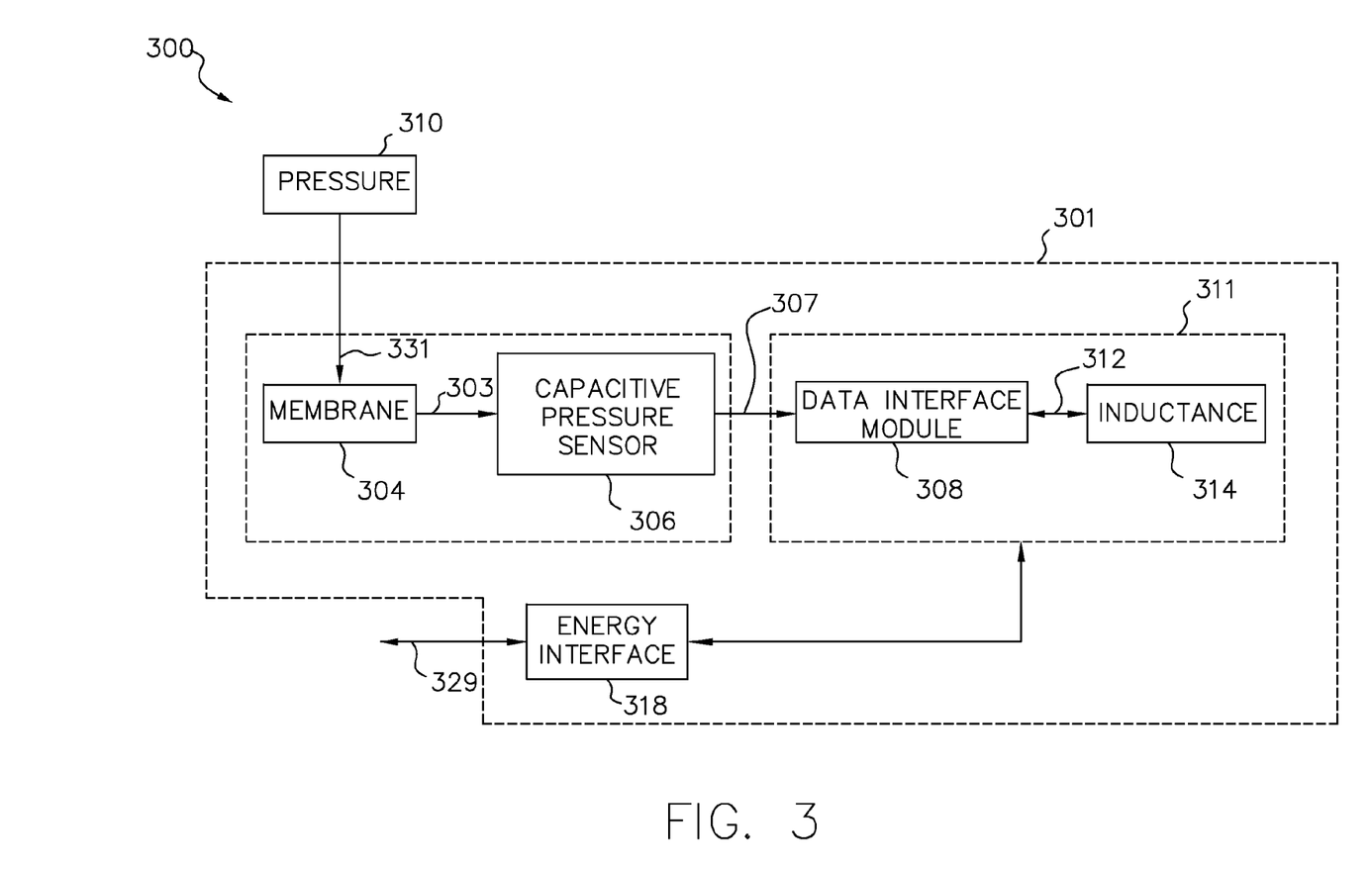
FIG. 3 is a block-diagram representation of a passive embodiment of a second energy transceiver system for use in the implantable device system of FIG. 1.

In one embodiment of the invention, the second energy transceiver system 200 may be fabricated as a purely passive component 300 of the implantable device system 100. In another example, the autocompensation channel 213 is not provided. A non-limiting example of such an embodiment, as shown in FIG. 3, may be realized when a physical parameter 310 to be sensed is a pressure that is available to a physical interface member 304 via a channel 331. The physical interface member 304 may be a membrane, which makes available the pressure to a sensor 306 via a channel 203. The sensor 306 may be a capacitive pressure sensor. The sensor 306 then makes available the value of the pressure obtained as a result of the pressure sensing operation to an energy transformer 311 via a channel 307. The energy transformer 311 includes a data interface module 308, which may be a capacitor whose capacitance is a function of the pressure value supplied to the energy transformer 311 by the sensor 306, and a transducer element 314, which may be an inductor. The data interface module 308 and the transducer element 314 are in contact via a channel 312 and effectively constitute a tank circuit having one or more resonant modes in which the periodically varying quantity can be an electric current, an electric charge, an electric voltage, or combinations thereof. The resonant modes that are activated depend on, among other factors, the value of the pressure made available to the energy transformer 311. The energy transformer 311 makes available, via a channel 327, the time dependence of the time varying quantity to an energy interface 318, which can communicate the same to the first energy transceiver system 102 in the form of electromagnetic radiation 329.

Figure 4:
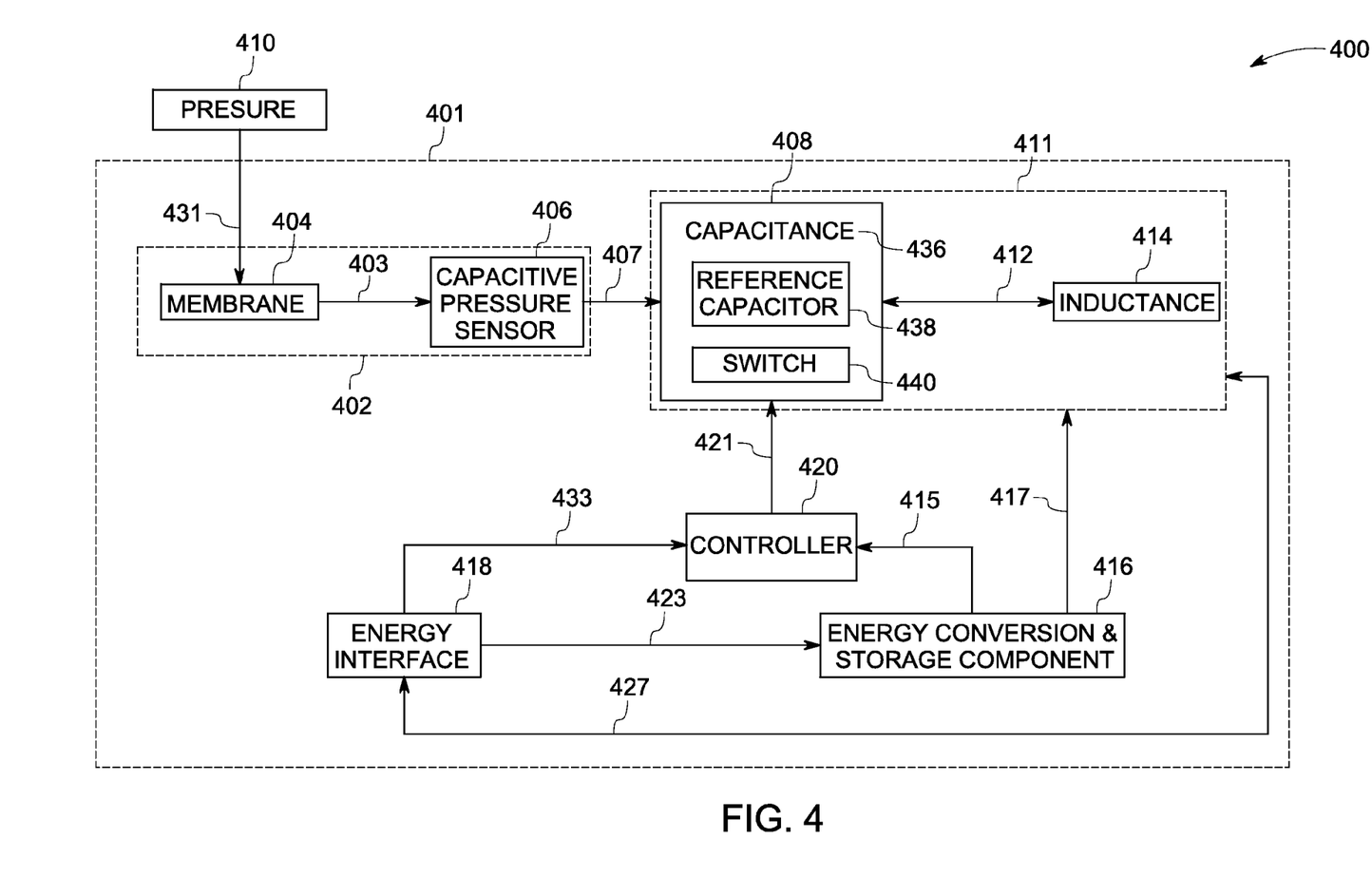
FIG. 4 is a block-diagram representation of a second energy transceiver system that contains an autocompensation enable line for use in the implantable device system of FIG. 1.

In one embodiment 400 of the invention, the second energy transceiver system 200 is provided with an autocompensation channel 421 (FIG. 4). A non-limiting example of such an embodiment may be realized when a physical parameter 410 to be sensed is a pressure. The physical parameter 410 is available at a physical interface via a channel 431. The physical interface member 404 may be a membrane, via which the pressure is sensed by a sensor 406, which in the present case is a capacitive pressure sensor. The physical interface member 404 can communicate with the sensor 406 via a channel 403. The sensor 406 then makes available a value of the pressure obtained as a result of the pressure sensing operation to a data interface module 408 via a channel 407. The data interface module 408 is a part of an energy transformer 411 and includes a variable capacitor 436, a reference capacitor 438, and a switch 440. The capacitance of the variable capacitor 436 is a function of the pressure value supplied to the data interface module 408 by the sensor 406. The switch 440 allows one to control the resonance modes, in for example, electric current electric voltage, or electric charge, of the energy transformer 411 by controlling whether or not the variable capacitor 436 and the reference capacitor 438 are in electromagnetic communication. The switch 440 in turn, places the variable capacitor 436 and the reference capacitor 438 in electromagnetic communication on the basis of autocompensating instructions it receives, via autocompensation channel 421 from the control component 420.

In one embodiment, the control component 420 is a switch controller. The control component 420 in turn receives autocompensation instructions from, for instance the first energy transceiver system 102, via an energy interface 418. In one embodiment, the energy interface may also be capable of communication with an energy conversion and storage component 416. In one embodiment of the invention, lines 415 and 417 are provided to aid the energy conversion and storage component 416 to provide energy to the control component 420 and the energy transformer 411, respectively. The energy conversion and storage component 416 further has the ability to supply energy to the control component 420. The other component of the energy transformer 411 is a transducer element 414, which may be an inductor. The data interface module 408 and the transducer element 414 are in contact via a channel 412 and effectively constitute a tank circuit having one or more resonant modes in which the periodically varying quantity can be an electric current, an electric charge, an electric voltage, or combinations thereof. The resonant modes that are activated depend on, among other factors, the value of the pressure made available to the energy transformer 411. The time dependence of the time varying quantity is communicated to the first energy transceiver system 102 via the energy interface 418. In one embodiment, the energy interface 418 is also capable of communicating with a control component via line 433.

In one embodiment, the energy conversion and storage component 416 may receive energy, via a line 423, from the energy interface 418. The energy interface 418 is also capable of two-way communication with the energy transformer 411 via a line 427. In one embodiment of the invention, the switch 440 that connects the reference capacitor 438 is connected in parallel with the variable capacitor 436. In another embodiment of the invention, the switch 440 that connects the reference capacitor 438 is connected in series with the variable capacitor 436. In yet another embodiment, the switch 440 switches between the reference capacitor 438 and the variable capacitor 436 by alternately connecting one or the other to the data interface module 408. Any or all of the capacitors discussed herein can refer to entities that are discrete or monolithic in time and/or space or can refer to entities that are distributed in time and/or space. Further, the parameters of the device system 100, such as charge distribution within the device system 100, that are affected by the presence of any or all of the capacitors discussed herein can be discrete and/or distributed in time and/or space.

The operation of the energy conversion and storage component 216, depending on the specific requirements imposed by the particular function that the implantable device system 100 is tasked to perform, may be based on a variety of sources of energy. Non-limiting examples of the sources of energy for the energy conversion and storage component 216 are nuclear, chemical, thermophotovoltaic, piezoelectric, solar, and combinations thereof.

In embodiments of the implantable device system 100, wherein the source of energy of the energy conversion and storage component 216 is electromagnetic, the energy may be received in wireless mode. In one embodiment, other components of the implantable device system 100 also may have the ability to receive energy in wireless mode. It will be appreciated that the ability of the components of the implantable device system 100 to receive energy in wireless mode will likely result in a simplification and enhanced reliability of the implantable device system 100.

The energy conversion and storage component 216 may be placed wholly or partially within organic tissues composing the patient, or it may be placed outside of the patient. Non-limiting examples of organic tissue where the energy conversion and storage component 216 may be placed include a gastrointestinal tract, a thorax, and an abdomen. The energy conversion and storage component 216 may also be placed subcutaneously. For instance, when the source of energy of the energy conversion and storage component 216 is solar, the energy conversion and storage component 216 may be placed subcutaneously.

In one embodiment of the invention, the energy conversion and storage component 216 includes an energy storage capacitor, a primary cell, a rechargeable battery, or combinations thereof. Suitable examples of energy storage capacitors include electrolytic capacitors and electric double layer capacitors (also known as ultracapacitors), super capacitors, and mechanical energy storage systems such as a spring. In one embodiment, electric double layer capacitors are used due to their enhanced energy storage capacity and environmental friendliness, as compared to capacitors based on traditional technologies. The rechargeable battery can employ any known technology that is suitable. Non-limiting examples of possible technologies that may be used include, nickel-iron, nickel-cadmium, nickel-metal hydride, nickel-zinc, lithium ion, lithium polymer, lithium sulphur, nano titanate, lithium iron phosphate, thin film lithium, zinc-bromine, vanadium redox, sodium sulphur, super iron, silver zinc, alkaline, and combinations thereof. Further, the energy conversion and storage component 216 may include semiconductor components and circuitry such as p-n junctions and transistors.

In one embodiment, the energy conversion and storage component 216 comprises an AC-DC converter, a rectifier, a voltage regulator, or combinations thereof. The AC-DC converter can be based on any suitable known technology, such as, for example, semiconductor controlled rectification. A non-limiting example of a converter based on such a technology is the silicon controlled rectifier.

Figure 5:
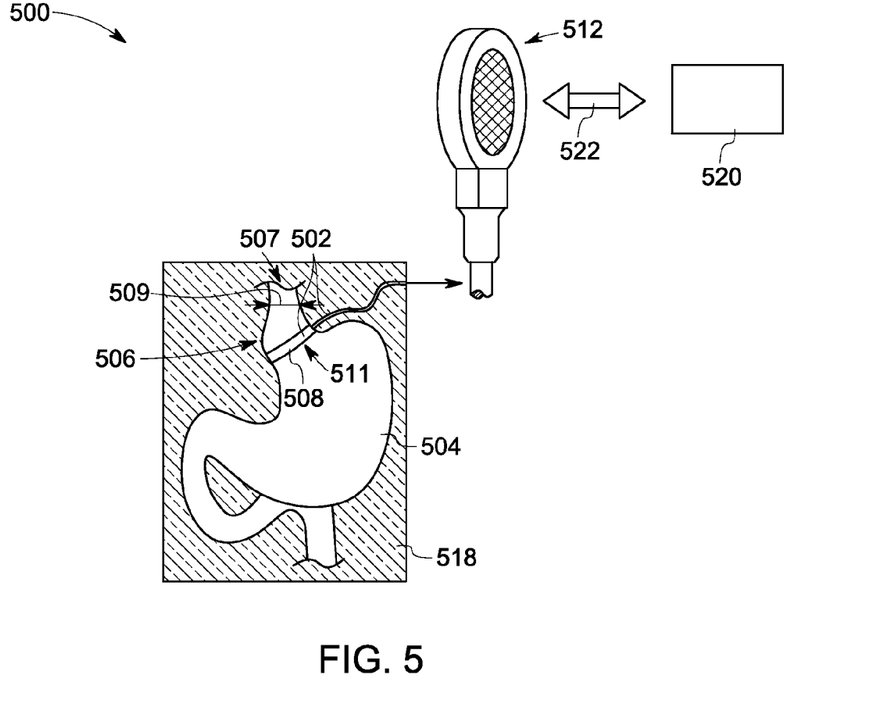
FIG. 5 is a schematic representation of an implantable device system in accordance with an exemplary embodiment of the invention.

In one embodiment 500 of the invention shown in FIG. 5, the implantable device system 100 serves as a gastrointestinal tract restriction device 502 containing at least one gastrointestinal tract restricting structure, such as the deformation member 508. FIG. 5 shows a gastrointestinal tract restriction device system 502 attached to a human stomach 504 in the vicinity of an esophagogastric junction 506 which contains an esophagogastric orifice 507 that has a cross-sectional area 509. The gastrointestinal tract restriction device system 502 further includes a deformation member 508. One end of the deformation member 308 mates with a sealable port 512. The sealable port 512 can be attached to the human body such that it is at least partially subcutaneous. As discussed further below, the sealable port 512 may facilitate non-invasive control of the cross-sectional area 509 of the esophagogastric orifice 507. The general viscera 518 surrounding the gastrointestinal tract restriction device 502 constitute an embodiment of the organic tissue 106.

The sealable port 512 can be any mechanical or electromechanical device that facilitates the introduction of fluids within the deformation member 508 when the deformation member 508 is in the form of a hollow tube. The sealable port 512, depending on its location within the implantable device system 502, may be composed of a biocompatible material. Non-limiting examples of materials from which the sealable port may be composed are, polymers, plastic materials, thermoplastic materials, and metals.

The introduced fluids can be any biocompatible liquid or gas. Non-limiting examples of fluids that may be introduced within the deformation member 508 when it is in the form of a hollow tube are isotonic salt solution, saline solution, and combinations thereof.

The embodiment illustrated in FIG. 5 contains a first energy transceiver system 102 (FIG. 1), and a second energy transceiver system 200 (FIG. 2) containing a physical parameter sensing system 202 (FIG. 2) and a transducer element 214 (FIG. 2). In one embodiment, the physical parameter sensing system 202 may perform a sensing operation of the physiological variable "pressure." Non-limiting examples of the types of measurements associated with the physiological variable "pressure" include measurement of a pressure wave at any location along the gastrointestinal tract that may be produced, for instance, due to peristaltic contractions induced due to food boluses in the gastrointestinal tract, or a strain in the gastrointestinal tract restriction device system 502, or a stress in the gastrointestinal tract restriction device system 502.

In one embodiment of the invention, the physical parameter sensing system 202 may detect flow of food through the gastrointestinal tract. The output of the physical parameter sensing system 202 that is available as input to the transducer element 214, would change as a result of such a flow of food. This in turn would result in a change in the output of the transducer element 214. This change in the output of the transducer element 214 may now be transmitted to the first electromagnetic transceiver system 102 as described earlier. Based on appropriate monitoring of the input to the first electromagnetic transceiver system 102, one may now instruct the gastrointestinal tract restriction device system 502 to induce a restriction in the gastrointestinal tract through a deformation of the deformation member 508. If such detection were to be performed continuously, then an appropriate deformation of the deformation member 508 can be induced only when food is being ingested. It will be appreciated that such a scheme will likely limit both the erosion of the tissue that is surrounded by the deformation member 508, and also may reduce energy consumption of the gastrointestinal tract restriction device system 502. It will be appreciated that the above feature would facilitate use of the gastrointestinal tract restriction device system 502 by a patients having, amongst other things, differing eating habits and needs.

The gastrointestinal tract restriction device system 502 can be used, for instance, to control the cross-sectional area 509 of the esophagogastric orifice 507. For instance, in one embodiment, the deformation member 508 partially or fully circumscribes the esophagogastric junction 506 to form a partial or complete "loop." The "interior" area 511, enclosed within the loop, may be changed by bringing about a suitable deformation of the deformation member 508. For instance, in one embodiment of the invention the deformation member 508 may be a hollow tube made of a pliant material that partially or fully circumscribes the esophagogastric junction 506 such that the loop that it forms has an initial area, and is in physical contact with, i.e., it embraces, the esophagogastric junction 506. It will be appreciated that any decrease in the interior area 511 of the loop will result in a decrease in the cross-sectional area 509 of the esophagogastric orifice 507. The size of the interior area 511 of the deformation member 508 (in this instant, of the hollow tube) may be decreased by pumping fluid (discussed below), via the sealable port 512, into the hollow tube. The pumping of the fluid into the hollow tube results in a build up of pressure within the hollow tube that can again be sensed ("monitored") via the physical parameter sensing system 202. The build up of pressure within the hollow tube results, because the hollow tube is made of pliant material, in a decrease in the interior area 511. On the other hand, a withdrawal of the fluid from the hollow tube 508, via the sealable port 512, will cause a decrease of pressure within the hollow tube, which will result in an increase in the interior area 511. In general the gastrointestinal tract restriction device system 502 can be attached at any other suitable location along the gastrointestinal tract of the patient.

In other embodiments of the invention the deformation member 508 may not be in the form of a hollow tube that utilizes introduction/removal and/or retention of fluid to change its shape and/or dimensions. It is conceivable that such a design may mitigate some of the risks, likely present in embodiments that contain a hollow tube and utilize fluids for their operation, associated with the possibility of leaking of the fluid through, for instance, the material composing the hollow tube.

The deformation member 508 can be composed of any material that is suitable for implantation within given organic tissue. Further, the deformation member 508 can be in any shape, and have any dimensions, that are appropriate for the given situation. For instance, as discussed herein, the deformation member 508 can be in the shape of a hollow tube. Also, any suitable mechanism, appropriate for the given material from which the deformable material 508 is composed, may be used to induce the deformation of the deformation member 508. For instance, if the deformation member 508 is composed of a shape memory alloy, Joule heating due to the passage of an electric current within the deformation member 508 may induce a deformation and/or change in tension, within the deformation member 508. The ability of the deformation member 508 to restrict the esophagogastric orifice 507 is therefore controllable via the thus induced deformation and/or the change in tension of the shape memory alloy from which it is composed.

In one embodiment of the invention, the deformation member 508 includes an electromagnetic material. The electromagnetic material can be so disposed that a passage of electric current through the electromagnetic material causes an attractive force to develop between the facing surfaces of the electromagnetic material, resulting in a decrease in the interior area 511 of the loop, which in turn can result in a decrease in the cross-sectional area 509 of the esophagogastric orifice. In another embodiment of the invention, permanent magnets may be disposed in order to be able to detect peristaltic movements in the gastrointestinal tract due to food intake.

It is likely that a restriction of the esophagogastric orifice 507 may result in a physiological feeling of satiation within in the patient. The gastrointestinal tract restriction device system 502 disclosed herein can be useful in the treatment of patients suffering from eating disorders such as compulsive overeating and bulimia nervosa. It may also be helpful in the treatment of, for instance, morbid obesity. On the other hand, it is conceivable that detection of multiple physiologic variables may be used to determine the amount of deformation ("corrective response") required of the deformation member 508. Embodiments of the invention may also incorporate multimodality therapy such as gastrointestinal tract restriction, in conjunction with other modalities such as neurostimulators, gastrointestinal tract muscle stimulators, gastrointestinal tract balloons, and bulking devices.

The deformation member 508 may include any thermally, electrically, or mechanically deformable material. Non-limiting examples of metallic materials from which the deformation member 508 may be composed include, nickel-titanium alloys, stainless steel, titanium, cobalt, chromium, and combinations thereof. Non-limiting examples of semiconducting materials from which the deformation member 508 may be composed include silicon. Non-limiting examples of elastic materials from which the deformation member 508 may be composed include silicone, polyurethane, silicone elastomer, polypropylene, Alloderm™ (available from, LifeCell Corporation, Delaware, One Millennium Way, Branchburg, N.J. 08876), Surgisis™ (available from, Cook Biotech, Inc., Indiana 1425 Innovation Place, West Lafayette, Ind. 47906), polyesters, poly-tetrafluoroethene (PTFE), polyvinylidene fluoride (PVDF), and polyester.

In one embodiment, the invention may include a pumping apparatus including a pump 520 and fluid communication line 522, capable of pumping fluid into or out of the hollow tube. For example, the pumping apparatus 518 may include one or more valves (not shown) and/or one or more motors (not shown), such as hydraulic or a pneumatic motors. The pumping apparatus is disposed so that it is capable of pumping fluid into or out of the hollow tube via for instance, the sealable port 512. The pumping apparatus may be capable of pumping fluid, in a step manner, or in a continuous manner, or in a combination of a step and a continuous manner. The pumping apparatus 518 may further include a fluid reservoir (not shown) connected to the motor, and having for instance, a variable volume.

In one embodiment of the invention, the physical parameter sensing system 202 is capable to measuring a pressure of the deformation member 508 when it is in the form of a hollow tube, when the pressure is within the range of about 200 milli meters of mercury to about 1550 milli meters of mercury. In another embodiment, the physical parameter sensing system 202 is capable to measuring the pressure of the elastic member 502 when the pressure is within the range of about 100 milli meters of mercury to about 300 milli meters of mercury. In yet another embodiment, the physical parameter sensing system 502 is capable to measuring the pressure of the elastic member 502 when the pressure is within the range of about 150 milli meters of mercury to about 400 milli meters of mercury.

In one embodiment of the invention, the second energy transceiver system 200 of the implantable device system 100 is housed in a biocompatible packaging 201. Non-limiting examples of materials from which such biocompatible packaging may be composed include, titanium, samarium cobalt, calcium oxide, cobalt oxide, polystyrenes, polyphosphoester, polyphosphazenes, aliphatic polyesters, natural polymers, or combinations thereof. The choice of the particular biomaterial used for a specific application is guided by host of considerations, including but not limited to, toxicological, biocompatibility, pathobiological, immune-response, specific anatomical site of implant, mechanical and/or electrical performance requirements, and ethical.

In one embodiment of the invention, the implantable system 100 has the ability to assess its own "state of health" based on some internal test routines and/or additional sensing modalities. It will be appreciated that such ability facilitates, in case of a malfunction, the diagnosis of the malfunction.

Figure 6:
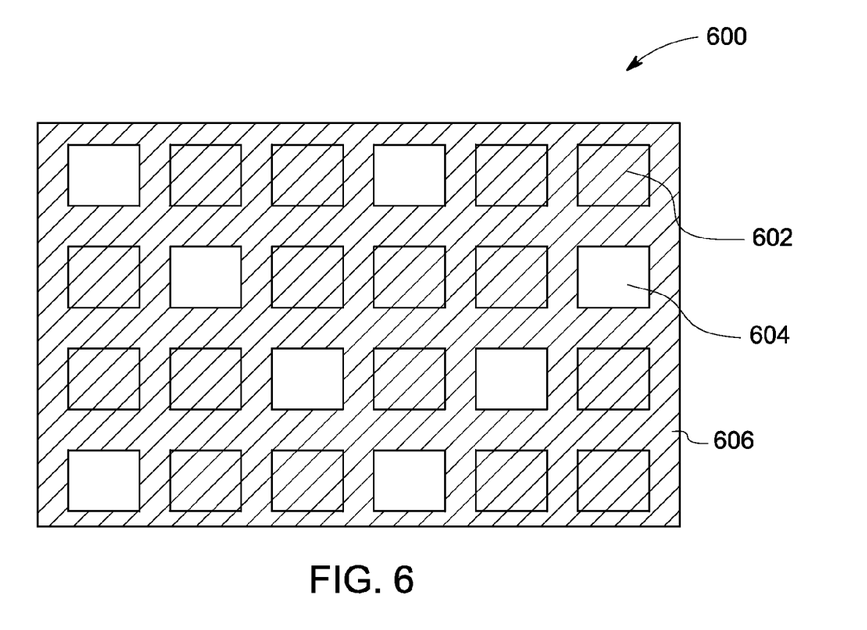
FIG. 6 is a schematic representation of an implantable device system array in accordance with an exemplary embodiment of the invention.

According to one embodiment of invention, an implantable device system array 600, as shown in FIG. 6, is disclosed. The implantable device system array 600 includes a plurality of transceiver systems, two examples of which are indicated via reference numerals 602 and 604, wherein each of the transceiver systems includes a first energy transceiver system (not shown), a second energy transceiver system (not shown) at least partially implanted within an organic tissue 606 and capable of communication with the first energy transceiver system, and a physical parameter sensing system (not shown) capable of communication with the second energy transceiver system and capable of performing a measurement operation of a physical parameter. In one embodiment of the invention, each of the plurality of transceiver systems is capable of independently communicating with any or all other transceiver systems of the plurality of transceiver systems comprising the array 600. In one embodiment of the invention, a medium between the plurality of transceiver systems that comprise the array 600 includes organic tissue 606. The plurality of transceiver systems comprising the array 600 may be fully or partially embedded within the organic tissue 606 as is indicated by the transceiver systems 602 and 604 respectively.

Figure 7:
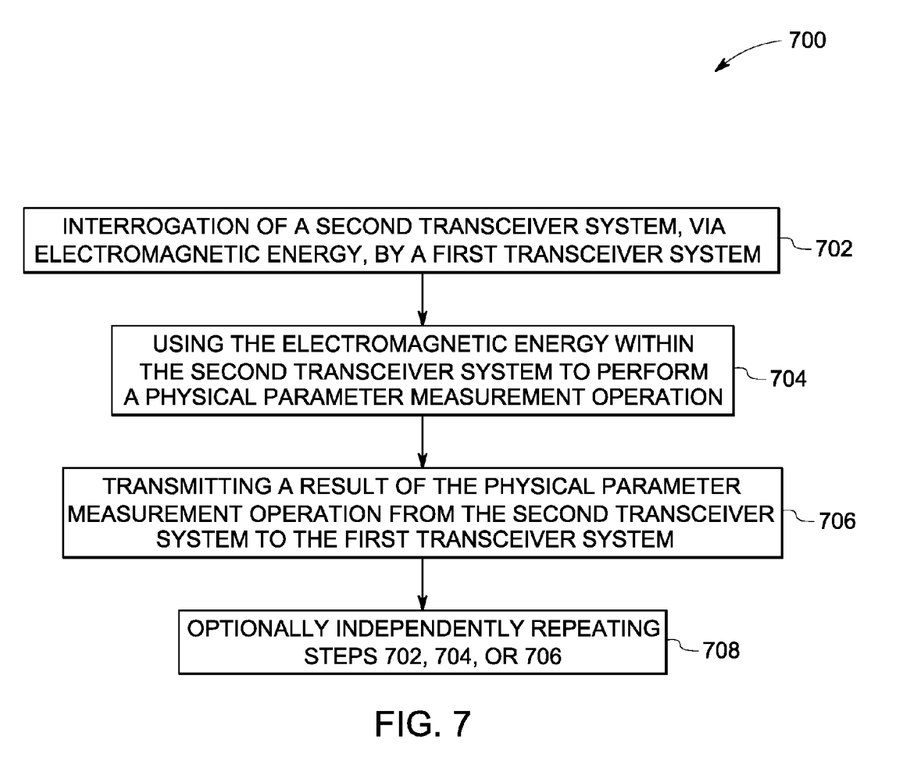
FIG. 7 illustrates a process flow of a physical parameter sensing operation in accordance with an exemplary embodiment of the invention.

A method 700 of monitoring a physical parameter is disclosed, as shown via the flow chart in FIG. 7. At step 702, the method 700 includes interrogation of a second transceiver system, via electromagnetic energy, by the first transceiver system. In one embodiment of the invention, the first and the second transceiver systems are substantially of the same type as the first energy transceiver system 102, and the second energy transceiver system 104 respectively. Further, as described herein, the electromagnetic energy may be used for the purpose of communication, or it may be used for the purpose of energizing components of the implantable device system 100. This is followed by step 704, which includes using the electromagnetic energy within the second transceiver system to perform a physical parameter measurement operation. In one embodiment of the invention, the physical parameter measurement operation may be performed by a physical parameter sensing system that is substantially of the same type as the physical parameter sensing system 202. The next step 706 includes transmitting a result of the physical parameter measurement operation from the second transceiver system to the first transceiver system. The next step 708 includes optionally independently repeating steps 702, 704, or 706, wherein the second transceiver system is at least partially implanted within an organic tissue and is capable of communication with the first transceiver system.

In one embodiment of the invention, the electromagnetic energy transmitted at step 702 and/or step 706 lies within a frequency range between about 75 kiloHertz to about 15 megaHertz. In one embodiment of the invention, the electromagnetic energy transmitted at step 702 and/or step 706 lies within a frequency range between about 400 kiloHertz to about 650 kiloHertz. In one embodiment of the invention, the electromagnetic energy transmitted at step 702 and/or 706 lies within a frequency range between about 125 kiloHertz to about 650 kiloHertz.

Figure 8:
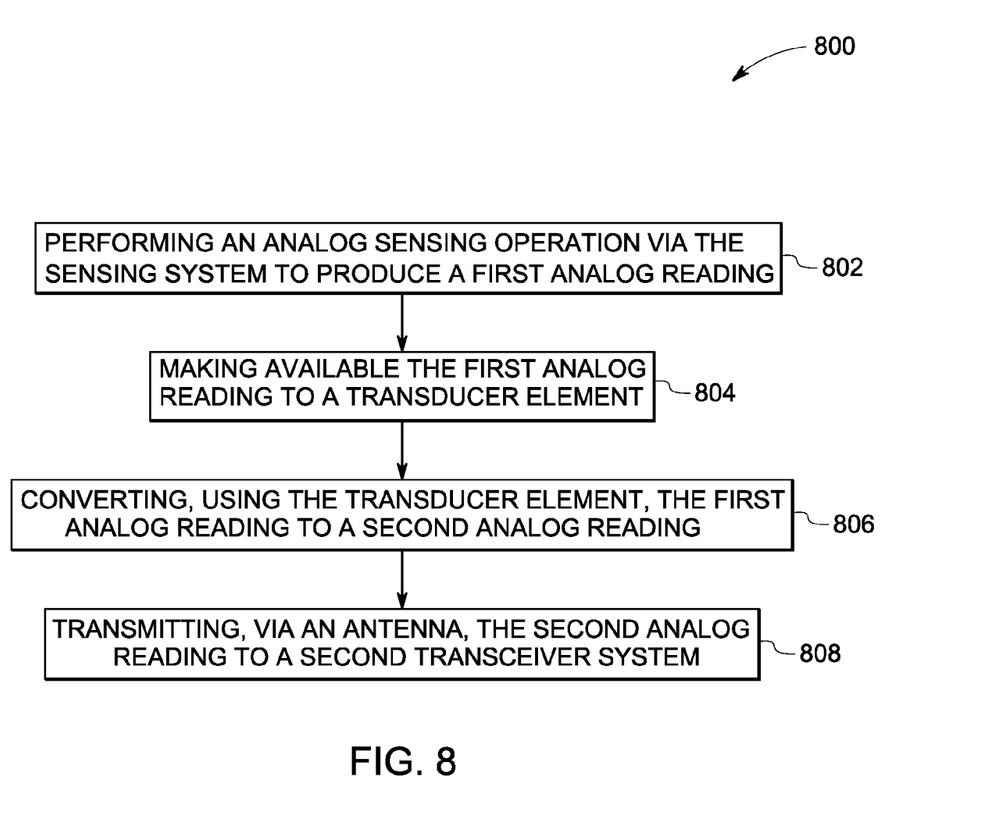
FIG. 8 illustrates a process flow of an interrogation operation in accordance with an exemplary embodiment of the invention.

According to one embodiment of the invention, a method 800 of performing a physical parameter measurement operation is disclosed, as shown via the flow chart of FIG. 8. The method 800 includes, at step 802, performing an analog sensing operation via the sensing system to produce a first analog reading. In one embodiment of the invention, the sensing system is substantially of the same type as the physical parameter sensing system 202. This is followed by step 804 that includes making available the first analog reading to a transducer element. In one embodiment, the transducer element is substantially of the same type as the transducer element 214. Next step 806 includes converting, using the transducer element, the first analog reading to a second analog reading. The next step 808 includes transmitting, via an antenna, the second analog reading to a second transceiver system. In one embodiment of the invention, the antenna is substantially of the same type as the energy interface 218. In one embodiment of the invention, the second transceiver system is substantially of the same type as the second energy transceiver system 104.

In one embodiment of the invention, it is possible to fabricate the implantable device system 100 without the use of any high permeability materials. It is likely that this capability enables the implantable device system to operate substantially unhindered even in the presence of magnetic fields, such as those that are encountered during magnetic resonance imaging scanning. It is possible that this capability enables the implantable device system 100 to operate within high magnetic fields of up to about 10 Tesla.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. An implantable device system comprising:
   a first energy transceiver system;
   a second energy transceiver system capable of being implanted and interrogated by the first energy transceiver system, wherein the second energy transceiver system comprises an energy transformer and a control component to control resonance modes of the energy transformer, wherein the control component comprises at least one of a switch controller, a position controller, and a reference controller;
   a sensing system, wherein a state of the sensing system is available at the second energy transceiver system;
   an elastic member; and
   a physical parameter sensing system capable of sensing a pressure acting on the elastic member.

2. The implantable device system of claim 1, wherein the first energy transceiver system and the second energy transceiver system are separated by a distance of up to about 15 cm.

3. The implantable device system of claim 1, wherein the physical parameter sensing system comprises a physical interface member, a sensor, and a data interface module.

4. The implantable device system of claim 3, wherein the physical interface member comprises a membrane.

5. The implantable device system of claim 3, wherein the sensor comprises a distributed sensor comprising a capacitive sensor.

6. The implantable device system of claim 3, wherein the sensor is capable of quantitatively detecting.

7. The implantable device system of claim 1, wherein the second energy transceiver system comprises
   an energy interface.

8. The implantable device system of claim 1, wherein the energy transformer comprises a data interface module and a transducer element.

9. The implantable device system of claim 8, wherein the data interface module comprises a capacitor.

10. The implantable device system of claim 8, wherein the transducer element comprises an inductor.

11. The implantable device system of claim 8, wherein the transducer element is capable of accepting an input quantity, wherein the input quantity comprises impedance.

12. The implantable device system of claim 1, wherein at least a part of the implantable device system is housed in a bio-compatible packaging comprising titanium, samarium cobalt, calcium oxide, cobalt oxide, polystyrenes, polyphosphoester, polyphosphazenes, aliphatic polyesters, natural polymers, or combinations thereof.

13. The implantable device system of claim 1, wherein the first energy transceiver system is selected from the list comprising an electromagnetic radiation transceiver, an acoustic energy transceiver, a mechanical energy transceiver, a vibration energy transceiver, and radiation transceiver.

14. The implantable device system of claim 1, comprising a pumping apparatus configured to pump fluid into or out of a hollow tube.

\* \* \* \* \*